United States Patent
Visweswara et al.

(10) Patent No.: US 11,883,161 B2
(45) Date of Patent: Jan. 30, 2024

(54) SWITCH CIRCUITRY FOR A FLUID MONITORING DEVICE

(71) Applicant: KONINKLIJKE PHILIPS N.V., Eindhoven (NL)

(72) Inventors: Ashoka Sathanur Visweswara, Amstelveen (NL); Mark Thomas Johnson, Arendonk (BE); Lutz Christian Gerhardt, Eindhoven (NL); Ron Martinus Laurentius Van Lieshout, Geldrop (NL)

(73) Assignee: Koninklijke Philips N.V., Eindhoven (NL)

(*) Notice: Subject to any disclaimer, the term of this patent is extended or adjusted under 35 U.S.C. 154(b) by 449 days.

(21) Appl. No.: 17/289,863

(22) PCT Filed: Oct. 30, 2019

(86) PCT No.: PCT/EP2019/079575
§ 371 (c)(1),
(2) Date: Apr. 29, 2021

(87) PCT Pub. No.: WO2020/089256
PCT Pub. Date: May 7, 2020

(65) Prior Publication Data
US 2021/0401346 A1    Dec. 30, 2021

(30) Foreign Application Priority Data
Oct. 31, 2018  (EP) .................................... 18203590

(51) Int. Cl.
*A61B 5/145*      (2006.01)

(52) U.S. Cl.
CPC ...... *A61B 5/14507* (2013.01); *A61B 5/14517* (2013.01)

(58) Field of Classification Search
CPC .. A61B 5/14507; A61B 5/14517; A61B 5/304
See application file for complete search history.

(56) References Cited

U.S. PATENT DOCUMENTS

| | | |
|---|---|---|
| 2011/0213217 A1 | 9/2011 | McKenna et al. |
| 2015/0112164 A1 | 4/2015 | Heikenfeld et al. |

(Continued)

FOREIGN PATENT DOCUMENTS

| | | |
|---|---|---|
| WO | 2016138087 A1 | 9/2016 |

OTHER PUBLICATIONS

International Search Report and Written Opinion, International Application No. PCT/EP2019/079575, dated Jan. 24, 2020.

(Continued)

*Primary Examiner* — Amanda K Hulbert

(57) ABSTRACT

According to an aspect, there is provided switch circuitry (1) for controlling power supplied to a fluid monitoring unit (4). The switch circuitry (1) comprises: a sensor (2) configured to detect fluid derived from the skin of a user and to generate a detection signal in response to detection of fluid; and a controller (3) configured to receive the detection signal, to generate a wake-up signal in accordance with the detection signal, and to supply the wake-up signal to a switch (6) controlling the power supply to the fluid monitoring unit (4) so as to activate the switch (6) and wake the fluid monitoring unit (4), wherein, optionally, the fluid is sweat. According to another aspect, there is provided method of controlling power to a fluid monitoring unit.

14 Claims, 7 Drawing Sheets

(56) References Cited

U.S. PATENT DOCUMENTS

| | | | | |
|---|---|---|---|---|
| 2016/0162256 | A1* | 6/2016 | Komaromi | H04Q 9/00 340/870.07 |
| 2016/0303558 | A1* | 10/2016 | Lehane | G01N 33/548 |
| 2018/0014787 | A1 | 1/2018 | Ganton et al. | |
| 2018/0035927 | A1 | 2/2018 | Cronin et al. | |

OTHER PUBLICATIONS

Dongwhi Choi, et al., "A smart pipet tip: Triboelectricity and thermoelectricity assisted in situ evaluation of electrolyte concentration", Nano Energy, vol. 38, 2017, pp. 419-427.

Hnin Yin Yin Nyein et al., "A Wearable Microfluidic Sensing Patch for Dynamic Sweat Secretion Analysis", ACS Sens. 2018, 3, 944-952.

Sonner, Z. et al. The microfluidics of the eccrine sweat gland, including biomarker partitioning, transport, and biosensing implications. Biomicrofluidics 9, (2015).

Sato, K., Kang, W. H., Saga, K. & Sato, K. T. Biology of sweat glands and their disorders. I. Normal sweat gland function. J. Am. Acad. Dermatol. 20, 537-63 (1989).

De Giovanni, N. & Fucci, N. The current status of sweat testing for drugs of abuse: a review. Curr. Med. Chem. 20, 645-61 (2013).

SCRAM Continuous Alcohol Monitoring | SCRAM Systems. Available at: https://www.scramsystems.com/products/scram-continuous-alcohol-monitoring/. (Accessed: Apr. 24, 2018).

Mena-Bravo, A. & Luque de Castro, M. D. Sweat: A sample with limited present applications and promising future in metabolomics. J. Pharm. Biomed. Anal. 90, 139-147 (2014).

Choi et al, A smart pipet tip: Triboelectricity and thermoelectricity assisted in situ evaluation of electrolyte concentration, Nano Energy, 2017, vol. 38, pp. 419-427.

Nanoduct Neonatal Sweat Analysis System | ELITechGroup. Available at: https://www.elitechgroup.com/product/nanoduct-neonatal-sweat-analysis-system/. (Accessed: Apr. 24, 2018).

Bandodkar, A. J. et al. Epidermal tattoo potentiometric sodium sensors with wireless signal transduction for continuous non-invasive sweat monitoring. Biosens. Bioelectron. 54, 603-9 (2014).

Rose, D. P. et al. Adhesive RFID Sensor Patch for Monitoring of Sweat Electrolytes. IEEE Trans. Biomed. Eng. 62, 1457-1465 (2015).

Guinovart, T., Valdés-Ramírez, G., Windmiller, J. R., Andrade, F. J. & Wang, J. Bandage-Based Wearable Potentiometric Sensor for Monitoring Wound pH. Electroanalysis 26, 1345-1353 (2014).

Gao, W. et al. Fully integrated wearable sensor arrays for multiplexed in situ perspiration analysis. Nature 529, 509-514 (2016).

Bandodkar, A. J. & Wang, J. Non-invasive wearable electrochemical sensors: A review. Trends Biotechnol. 32, 363-371 (2014).

Van Dam, R. Solvent-resistant elastomeric microfluidic devices and applications. (2006).

Choi, J., Kang, D., Han, S., Kim, S. B. & Rogers, J. A. Thin, Soft, Skin-Mounted Microfluidic Networks with Capillary Bursting Valves for Chrono-Sampling of Sweat. Adv. Healthc. Mater. 6, 1-10 (2017).

Kim, S. B. et al. Super-Absorbent Polymer Valves and Colorimetric Chemistries for Time-Sequenced Discrete Sampling and Chloride Analysis of Sweat via Skin-Mounted Soft Microfluidics. Small 1703334, 1703334 (2018).

Ileperuma, W. R. K., Sun, J.-Y., Suo, Z. & Vlassak, J. J. Force and stroke of a hydrogel actuator. Soft Matter 9, 8504 (2013).

Begam, T., Nagpal, A. K. & Singhal, R. A comparative study of swelling properties of hydrogels based on poly (acrylamide-co-methyl methacrylate) containing physical and chemical crosslinks. J. Appl. Polym. Sci. 89, 779-786 (2003).

Ehrenhofer, A., Elstner, M. & Wallmersperger, T. Normalization of hydrogel swelling behavior for sensoric and actuatoric applications. Sensors Actuators B. Chem. 255, 1343-1353 (2018).

Bandodkar, Amay J., et al. "Soft, stretchable, high power density electronic skin-based biofuel cells for scavenging energy from human sweat." Energy & Environmental Science 10.7 (2017): 1581-1589.

* cited by examiner

Scheme 1.

SWITCH CIRCUITRY FOR A FLUID MONITORING DEVICE

This application is the U.S. National Phase application under 35 U.S.C. § 371 of International Application No. PCT/EP2019/079575, filed on 30 Oct. 2019, which claims the benefit of European Application Serial No. 18203590.7, filed 31 Oct. 2018. These applications are hereby incorporated by reference herein.

FIELD OF THE INVENTION

Embodiments of the present invention relate generally to controlling power supplied to a fluid monitoring device.

BACKGROUND OF THE INVENTION

Non-invasive, continuous and prolonged monitoring of biomarkers that indicate health and well-being is in demand. For example, for monitoring dehydration, stress, sleep, children's health and in perioperative monitoring. Bodily fluids derived from the skin, such as sweat, sebum and interstitial fluid, may be used in monitoring. For example, sweat is a non-obtrusively accessible bio-fluid containing physiologically and metabolically rich information. The development of reliable sweat sensing has been hampered by several issues: (1) results from sweat sensing have been highly variable; (2) a correlation between blood and sweat values appears to be lacking for various biomarkers; (3) the focus of sweat sensing has been on sensors, not on reliable and robust collection methods for the minute amounts produced. Some examples of clinical relevant components of sweat are: Na+, Cl− and/or K+ to monitor dehydration; Lactate as early warning for inflammation; glucose for diabetics & neonates; and cortisol for sleep and stress monitoring.

Sweat based continuous monitoring electronics, such as wearable patches, are often battery powered, with power required by the electronics to process, analyse and communicate data measured by sweat sensors. Power consumption of such electronics is highly significant, in particular due to the continuous monitoring and user convenience. Sub-optimal power management in such devices can lead to frequent recharging of the device and/or replacement of the device, causing inconvenience to the user, and/or an increase in the required battery size, increasing the footprint cost, weight, etc. of the wearable device, which also inconveniences the user.

It is therefore desirable to minimise the power consumption of the electronics and efficiently manage the power consumed by the fluid monitoring electronics.

SUMMARY OF THE INVENTION

According to an embodiment of a first aspect, there is provided switch circuitry for controlling power supplied to a fluid monitoring unit, the switch circuitry comprising: a sensor configured to detect fluid derived from the skin of a user and to generate a detection signal in accordance with detection of fluid; and a controller configured to receive the detection signal, to generate a wake-up signal in accordance with the detection signal, and to supply the wake-up signal to a switch controlling the power supply to the fluid monitoring unit so as to activate the switch and wake the fluid monitoring unit, wherein, optionally, the fluid is sweat.

Accordingly, the power supplied to the fluid monitoring unit may be controlled in accordance with the detection of fluid. That is, power may be supplied to the fluid monitoring unit when fluid is detected by the sensor such that the fluid monitoring unit is active when there is fluid present to be analysed. Conversely, power may not be supplied to the fluid monitoring unit when there is no fluid or an insufficient amount of fluid detected, and so the fluid monitoring unit may consume little or no power during periods when there is no fluid on which to perform monitoring. The fluid may optionally be sweat. The sensor may detect bodily fluids excreted and derived from the skin of the user.

The sensor may preferably detect sweat. That is, the sensor may be configured to detect sweat and to generate a detection signal in accordance with detection of sweat. If the senor is configured to detect sweat, then the fluid monitoring unit may be a sweat monitoring unit.

The power consumption of the fluid monitoring unit may therefore be reduced and limited to occasions when bodily fluids derived from the skin of the user, such as sweat, is present. That is, at times when there is no fluid present, there is nothing for the fluid monitoring unit to measure/monitor and so there is no need for the fluid monitoring unit to be active and power consumed by the unit will be wasted. Thus, by controlling the power supplied to the fluid monitoring unit in accordance with the detection of fluid, the power consumption of the unit may be appropriately limited and the lifespan of the power source, for example, a battery, may be maximised.

The sensor generates the detection signal in accordance with the detection of fluid. For example, the sensor may generate the detection signal in response to detecting fluid, an amount of fluid and/or a property of detected fluid. The detection signal may be an electric potential that is generated by the sensor directly from the detection of fluid. That is, the detection of fluid may generate a voltage which is used as the detection signal and provided to the controller. The sensor may be a wet detector provided in a microfluidic path which collects fluid. The wet detector may be adapted to emit a wetting signal when a change of humidity is present in the microfluidic path (beyond a humidity threshold value) as the detection signal. As discussed above, the fluid may be sweat and so the sensor may detect sweat.

Thus an electric signal (potential) generated by the sweat detection is utilised to wake and activate the fluid monitoring unit. The electric signal may be generated in a number of ways depending on the configuration and/or type of the sensor. That is, the conditions for the generation of the electric signal may vary in accordance with the sensor and/or what the sensor is specifically detecting. The detection signal may correspond to the potential generated by the sensor in response to the detection such that the detection signal may be, or may be generated using, the generated voltage. The detection signal may be considered as the output of the sensor, which is input to the controller.

The fluid monitoring unit may monitor bodily fluids derived from the skin of the user, such as, for example, sweat, sebum and interstitial fluid, and is associated with the continuous monitoring of a user and, in particular, the fluid of a user and/or properties of the fluid of the user. If the fluid monitoring unit monitors sweat, then the unit may be referred to as a sweat monitoring unit. The sweat monitoring unit may also be referred to as sweat monitoring electronics or a sweat monitoring device, and is associated with the continuous monitoring of a user and, in particular, the sweat of a user and/or properties of the sweat of the user. For simplicity, the monitoring of fluids and the fluid monitoring unit may be referred to in this specification as the monitoring of sweat and the sweat monitoring unit. However, it is noted that embodiments of the present invention are not limited to the monitoring of sweat or the sweat monitoring unit, and any bodily fluids excreted and derived from the skin of the user may be monitored.

Monitoring may comprise acquiring measurements from excreted fluid. The fluid monitoring unit may be provided as a wearable device that is attached to the user at a suitable location. This may be a location with a high expected amount of sweat glands. The location of the fluid monitoring unit may be referred to as a measuring/measurement site. The sensor may comprise a sample site which is the site at which the detection of fluid occurs. The sample site of the sensor may be positioned in close proximity to the measuring/measurement site of the fluid monitoring unit so that the amount of fluid at each site is comparable. The properties and requirements of the fluid monitoring unit, for example, the optimum amount of fluid, may vary according to the application of the unit and/or the properties of the fluid to be monitored.

The user is an individual whose fluid is to be monitored by the fluid monitoring unit. The user may also be referred to as a patient, human subject, individual, person of interest, etc. and may be an individual whose fluid is being monitored to assess their health and well-being. Sweat glands are arranged in the skin such that they excrete sweat out of the surface of the skin of the user. Glands that excrete sweat may be considered to be active glands, such that if no sweat is excreted at a particular area of the skin, it is considered that there are no glands or no active glands at that area.

The switch is configured to control the power supplied to the fluid monitoring unit. The switch may connect or disconnect the fluid monitoring unit with a power supply in accordance with the receipt of the wake-up signal. The switch may be provided as a separate component in the system, for example, disposed between the power supply and the fluid monitoring unit. The switch may also be part of the fluid monitoring unit, such as an on/off or power switch. The switch may also be provided as part of the switch circuitry, such that the switch acts as an interface between the power supply and the fluid monitoring unit. The switch may, for example, be a transistor, such as a MOSFET.

It may be seen that when the switch is activated, power is supplied to the fluid monitoring unit. Conversely, it may be seen that when the switch is not activated, power is not supplied to the fluid monitoring unit or a reduced amount of power is supplied to the fluid monitoring unit, such that the unit is not awake. That is, the fluid monitoring unit may be in a sleep or low power consumption mode when the switch is not activated. It may be considered that the switch is closed when activated and open when deactivated. The switch is closed by the wake-up signal and may conversely be opened in response to the wake-up signal not being applied to the switch. Accordingly, the fluid monitoring unit may enter the sleep or low power mode when the sensor does not supply the detection signal to the controller, for example, when there is no fluid detected by the sensor. That is, the wake-up signal may not be supplied to the switch by the controller and so the switch is deactivated. Thus, the power consumed by the fluid monitoring unit when there is no fluid to be analysed may be minimised and the lifespan of the power source, for example, a battery, may be maximised.

The controller receives the detection signal from the sensor, generates the wake-up signal and provides it to the switch. Thus, it may be seen that the controller is the interface between the detection of fluid and the control of power to the fluid monitoring unit. The controller may also receive signals, such as parameters and settings from the fluid monitoring unit. Thus, the controller may be directly connected to the sensor, the switch and the fluid monitoring unit. The power consumption of the controller may be low and lower than that of the fluid monitoring unit when the unit is awake and the overall power consumption of the switch circuitry is reduced by controlling the power supplied to the fluid monitoring unit. The controller may also be referred to as a low power wake-up generation block.

The fluid monitoring unit may preferably generate a timer signal indicating a timer delay in response to receiving the wake-up signal and supply the timer signal to the controller. The controller may be configured to supply the wake-up signal to the switch for the duration of the timer delay indicated by the timer signal so as to maintain activation of the fluid monitoring unit for at least the duration of the timer delay. The timer signal may therefore ensure that power is supplied to the fluid monitoring unit for a minimum amount of time, corresponding to the timer delay, even if the detection signal is no longer supplied to the controller. Thus the timer signal or the detection signal may trigger/maintain activation of the fluid monitoring unit.

The sensor may generate the detection signal in response to detecting a predetermined amount of fluid for a predetermined amount of time. That is, the detection signal may be generated when an amount of fluid exceeding a predetermined threshold is detected. The sensor may also delay generating the detection signal, such that it is only generated when an amount of fluid is detected for a time period exceeding a predetermined threshold. Thus, it may be ensured that the detection signal is only generated when an appropriate amount of fluid is detected and/or the fluid is detected for an appropriate amount of time. The amount of fluid and/or time required to generate the detection signal may be dependent on properties of the fluid monitoring unit, such as the fluid required for the unit to perform meaningful monitoring, thereby avoiding waking the monitoring unit when there is an amount of fluid that is insufficient for the monitoring unit to perform the required monitoring.

The switch circuitry may also comprise a notification unit configured to receive the wake-up signal and to generate an alarm in response to receiving the wake-up signal. The alarm may be any suitable alarm or notification and may notify a user that the fluid monitoring unit has been activated. The alarm may be audio and/or visual, for example, a notification on a user display may be generated as the alarm.

The sensor may preferably be configured to be positioned in contact with the skin of a user so as to detect fluid excreted from the skin of the user. That is, the sensor may be directly attached or connected to the surface of the skin to directly detect fluid excreted by fluid glands at the surface of the skin. For example, the sensor may be provided as a patch-like structure or as part of such a structure that may attach directly to the skin of the user whose sweat is to be monitored by the fluid monitoring unit.

The sensor may be arranged to be positioned at a certain location of the body to detect the fluid excreted from the skin of the user. The sensor may be positioned in close proximity to the fluid monitoring unit and/or at a location at which there is a high probability of fluid excretion. The sensor may be provided with adhesive for attaching the sensor to the skin of the user. Positioning the sensor in contact with the skin may increase the accuracy of the fluid detection and ensure that the detection is reflective of the condition of the user, in particular the fluid excretion of the user.

The sensor may, additionally or alternatively, detect a first amount of fluid at a first time point; and detect a second amount of fluid at a second time point occurring after the first time point. The sensor may then calculate a difference between the first amount of fluid and the second amount of fluid and generate the detection signal when the difference between the first amount of fluid and the second amount of fluid exceeds a predetermined threshold. The sensor may therefore generate the detection signal in accordance with a change in the amount of fluid detected over a period of time, i.e. based on the rate of change of the amount of fluid detected rather than the magnitude of the amount of fluid at a single point in time. Conversely, if the detection signal is provided to the controller such that the fluid monitoring unit is awake, then the sensor may cease providing the detection signal to the controller when the difference between the first amount of fluid and the second amount of fluid does not exceed a predetermined threshold. Thus, the fluid monitoring unit may go to sleep if the fluid has not sufficiently changed over time. References to the first amount of fluid at a first time point and a second amount of fluid at a second time point may, more specifically, be considered as levels of voltage signals generated in response to the amount of fluid detected at the respective time points. Thus, in practice, the difference between voltage generated at the first time point and voltage generated at the second time point may be calculated.

According to a preferred embodiment of an aspect, the sensor may be configured to measure a concentration of a substrate in the detected fluid; and generate the detection signal when the concentration of the substrate in the detected fluid exceeds a predetermined threshold. The substrate may, for example, be lactate, such that the sensor may be configured to measure lactate concentration of detected sweat; and generate the detection signal when the lactate concentration of the detected sweat exceeds a predetermined threshold. That is, the detection signal may be generated in accordance with the concentration of the lactate or other substrates in the detected sweat, such that the fluid monitoring unit may be activated when a given concentration of lactate (substrate) is present in the sweat. The electric signal generated in accordance with the detection of sweat may therefore directly correspond to the concentration of lactate in the sweat.

The sensor may also be configured to measure the concentration of one or more enzymes resulting from the fluid. The enzymes may not be found in fluid but convert a substrate into a product, whereby energy is produced. For example, the conversion of glucose and oxygen by glucose oxidase gives a product with $H_2O_2$ (hydrogen peroxide) which can donate an electron to the electrode. Such other enzymes include, but are not limited to, glucose oxidase, choline oxidase, cholesterol oxidase, D-amino and L-amino acid oxidase, alcohol oxidase, uricase, lactate oxidase, xanthine oxidase, bilirubin oxidase, glutamate oxidase, putrescine oxidase and polyamine oxidase. Thus generation of the detection signal may be based on the detection of fluid and/or properties of the detected fluid, such as the lactate concentration. This may be beneficial, for example, if the fluid monitoring unit is observing a property of sweat that is correlated with the lactate concentration of the sweat, or the concentration of an enzyme. Similarly, the fluid monitoring unit may consider enzymes associated with the sweat.

Generation of the detection signal by the sensor may be triggered by any one of a plurality of conditions, such as the conditions discussed above. Two or more of these conditions may be used in cooperation to ensure that the detection signal is appropriately generated, for example, based on the application of the switch circuitry. The condition for generating the detection signal may also depend on which biomarker of the fluid is to be monitored. For example, observation of some biomarkers in fluid may require a greater amount of fluid than other biomarkers. If a component being measured has a high resorption rate, then measurement at a high fluid rate may be preferable to reduce the variation on the signal.

The conditions for generating the detection signal may also dynamically change in accordance with the history of the activation of the fluid monitoring unit. For example, if the fluid monitoring unit has been active in a recent predetermined time period, then generation of the detection signal by the sensor may be based on the change in the amount of fluid over a time period, rather than the magnitude of the amount of fluid. Alternatively, generation of the detection signal may be suppressed such that the fluid monitoring unit does not perform repeat monitoring of the fluid in two periods of time that are very close. The controller may be configured to set the requirements for generation of the detection signal by the sensor. The controller may also be configured to store an activation history of the fluid monitoring unit, the activation history indicating generation of the wake-up signal over time. The controller may also be configured to set the requirements for generation of the detection signal by the sensor based on the activation history.

The switch circuitry may further comprise a variable resistor connected in parallel with the sensor; and a capacitor connected in parallel with the variable resistor. The variable resistor and the capacitor may control the delivery of the detection signal to the controller. In other words, a variable resistor and a capacitor may both be provided in parallel across the output of the sensor and between the sensor and the controller to optimise the timing of the detection signal delivery to the controller based on the rate of fluid generation. The parallel connected variable resistor may provide dynamic and configurable resistance to the sensor output. The value of the resistor may be controlled to control the charging of the capacitor and charging of the capacitor may delay the delivery of the detection signal to the controller and so the resistor and capacitor may provide a configurable delay. Accordingly, by varying the time taken for the capacitor to charge, the time taken for the detection signal to be delivered may be controlled. Waking of the fluid monitoring unit may therefore be based on the rate of fluid generation.

Furthermore, the value of the resistor and thus the voltage required to charge the capacitor may effectively define a threshold voltage which needs to be met before the detection signal is provided to the controller. That is, the generated voltage may have to exceed a given value in order to charge the capacitor and deliver the detection signal to the controller. If the detection signal is generated in accordance with the amount of fluid detected, then it may be seen that the threshold will relate to a given amount of fluid being detected. The resistor and capacitor may also act as a filter to prevent transient signals from activating the fluid monitoring unit when a suitable amount of fluid has not been detected by the sensor.

The value of the variable resistor may be controlled by the controller. The controller may control the value of the variable resistor in accordance with parameters received from the fluid monitoring unit when the fluid monitoring unit is active. That is, when the fluid monitoring unit is active, it may provide information to the controller indicating parameters which the value of the variable resistor may be controlled in accordance with. The parameters may be parameters of the fluid monitoring unit and/or parameters of the user. That is, the value of the variable resistor may be controlled based on properties of the fluid monitoring electronics, for example, the property of the fluid being monitored, the type of measurement and/or an amount of fluid required by the fluid monitoring electronics. The value may additionally or alternatively be controlled based on conditions of the user to be monitored, such as, for example, the sweat rate of the user. The variable resistor may be provided as a MOSFET and the controller may control the value of the resistance provided by the MOSFET by controlling switching of the MOSFET.

The controller may temporarily set the variable resistor to a minimum value prior to deactivating the switch so as to discharge the capacitor. That is, the resistor may be set to a low value of resistance so that the capacitor may be discharged and that the delay/threshold set by the capacitor and resistor may be effectively 'reset'. This may occur at the end of a period in which the fluid monitoring unit has been active, i.e. while the fluid monitoring unit is awake and before it is to return to the sleep mode by deactivating the switch. The capacitor may be discharged at the end of a period of time corresponding to an analysis cycle by the fluid monitoring unit, which may be referred to as a measurement cycle, i.e. the measurement cycle may be a period of time when the fluid is analysed by the fluid monitoring electronics. The resistor may be set to a low value temporarily such that it is set low for a period of time to allow the capacitor to discharge before the resistor is set to a value corresponding to the desired delay/voltage threshold discussed above.

The sensor may be an electronic skin based bio-fuel cell, E-BFC, that generates an electric potential in response to the detection of fluid. The generated electric potential may correspond to the amount of fluid detected. The electric potential may be or may be used to generate the detection signal, such that generation of the detection signal corresponds to the generation of the electric potential in response to the detection of fluid. Thus, the generated electric potential (voltage) may be used to wake the fluid monitoring unit, via the controller and the switch controlling the power supply to the unit. The potential generated by the E-BFC may be proportional to the amount of fluid detected such that a greater amount of fluid results in a larger generated potential.

The E-BFC may generate the detection signal when the generated electric potential exceeds a predetermined threshold corresponding to the detection of a given amount of fluid. The generated electric potential may be the detection signal and so the signal may not be supplied to the controller until a threshold value, corresponding to a minimum amount of fluid, has been generated. A minimum amount of fluid may therefore be required before the detection signal is generated, or provided to the controller. Waking of the fluid monitoring unit may therefore require detection of a minimum amount of fluid.

The sensor may generate the detection signal in response to the flow of fluid through the device. The sensor may comprise: a flow channel arranged such that fluid flows through the flow channel; and an induction electrode (array) arranged circumferentially around the periphery of the flow channel. The induction electrode (array) may generate a triboelectric potential due to moving ions in the fluid flowing through the flow channel. The triboelectric potential generated by the induction electrode may correspond to the rate of moving ions in the fluid flowing through the flow channel. More specifically, to the velocity and concentration (flow rate and concentration rate) of moving ions in the fluid flowing through the flow channel. The induction electrode may generate the detection signal when the generated triboelectric potential exceeds a predetermined threshold corresponding to a given rate of moving ions. Thus moving ions in the fluid may be used to provide the detection signal. The ions moving through the flow channel may interact with the induction electrode to induce a triboelectric potential (voltage).

The triboelectric potential may be or may be used to generate the detection signal, such that generation of the detection signal corresponds to the generation of the triboelectric potential in response to fluid flowing through the flow channel. Thus, the generated triboelectric potential (voltage) may be used to wake the fluid monitoring unit, via the controller and the switch controlling the power supply to the unit. The potential generated by the fluid flowing in the flow channel and measured with the induction electrode may be proportional to the amount of fluid detected such that a greater amount of fluid results in a larger generated potential. Thus, a minimum flow of fluid may be required before the detection signal is generated or supplied to the controller and the fluid monitoring unit is activated. The flow channel may be a microfluidic path.

The generated triboelectric potential may also be monitored over time such that the detection signal is generated in response to a change in the triboelectric potential. That is, the sensor may detect a first amount of triboelectric potential at a first time point; and detect a second amount of triboelectric potential at a second time point occurring after the first time point. The sensor electronics may then calculate a difference between the first amount of triboelectric potential and the second amount of triboelectric potential and generate the detection signal when the difference between the first amount of triboelectric potential and the second amount of triboelectric potential exceeds a predetermined threshold. Conversely, if the detection signal is provided to the controller such that the fluid monitoring unit is awake, then the sensor may cease providing the detection signal to the controller when the difference between the first amount of triboelectric potential and the second amount of triboelectric potential does not exceed a predetermined threshold. Thus, the fluid monitoring unit may go to sleep if the triboelectric potential has not sufficiently changed over time. Similarly, the fluid monitoring unit may go to sleep if, in the case of a single-ended measurement against earth as a reference electrode, the triboelectric potential falls below an absolute threshold value if measured against ground.

The induction electrode may, for example, be arranged in series as circumferential elements/arrays of the flow channel such that, if a plurality of induction electrodes are provided, the fluid flows between a pair of induction electrodes. The induction electrode may be measured against ground. There may preferably be provided at least two induction electrodes: a positive electrode and a grounded electrode or reference electrode. The triboelectric potential generated at the induction electrodes may correspond to the differential between the two electrodes and may provide the detection (activation) signal to the switch of the power control unit (controller).

Alternatively, the sensor may comprise: a flow channel arranged such that fluid flows through the flow channel; and one or more ion-selective electrodes arranged inside the flow channel. The ion-selective electrode may generate an electrochemical potential due to moving ions in the fluid flowing through the flow channel. The electrochemical potential generated by the ion-selective electrode may correspond to the rate or concentration of (specific) moving ions in the fluid flowing through the flow channel. The ion-selective electrode may generate the detection signal when the generated electrochemical potential exceeds a predetermined threshold corresponding to a given rate or concentration of moving ions. Thus (specific) moving ions in the fluid may be used to provide the detection signal. The ions moving through the flow channel may interact with the ion-selective electrode to induce an electrochemical potential (voltage).

The electrochemical potential may be or may be used to generate the detection signal, such that generation of the detection signal corresponds to the generation of the electrochemical potential in response to fluid flowing through the flow channel. Thus, the generated electrochemical potential (voltage) may be used to wake the fluid monitoring unit, via the controller and the switch controlling the power supply to the unit. The potential generated by the ion-selective electrode and the fluid flowing in the flow channel may be proportional to the amount of fluid and/or concentration of specific ions detected such that a greater amount of fluid and/or greater concentration of specific ions results in a larger generated potential. Thus, a minimum flow of fluid may be required before the detection signal is generated or supplied to the controller and the fluid monitoring unit is activated. The flow channel may be a microfluidic path.

The generated electrochemical potential may also be monitored over time such that the detection signal is generated in response to a change in the electrochemical potential. That is, the sensor (and, more specifically, control electronics and software associated with the sensor) may detect a first amount of electrochemical potential at a first time point; and detect a second amount of electrochemical potential at a second time point occurring after the first time point. The sensor may then calculate a difference between the first amount of electrochemical potential and the second amount of electrochemical potential and generate the detection signal when the difference between the first amount of electrochemical potential and the second amount of electrochemical potential exceeds a predetermined threshold. Conversely, if the detection signal is provided to the controller such that the fluid monitoring unit is awake, then the sensor may cease providing the detection signal to the controller when the difference between the first amount of electrochemical potential and the second amount of electrochemical potential does not exceed a predetermined threshold. Thus, the fluid monitoring unit may go to sleep if the electrochemical potential has not sufficiently changed over time.

The ion-selective electrode and reference electrode may be (concentrically) arranged in the flow channel such that the fluid flows around the reference electrode. There may preferably be provided at least two ion-selective electrodes: a positive electrode and a grounded electrode or reference electrode. The generated signal of the ion-selective electrode may be measured against the (potential on the) reference electrode. The fluid may flow through the ion-selective membrane electrode and the electrode may be comparable to a potentiometric pH measurement probe using a reference potential/solution.

The present invention extends to method aspects corresponding to the device aspects.

In particular, according to an embodiment of a second aspect, there is provided a method of controlling power to a fluid monitoring unit, the method comprising: detecting fluid derived from the skin of a user; generating a detection signal in accordance with the detection of fluid; generating a wake-up signal in accordance with the detection signal; and supplying the wake-up signal to a switch controlling the power supply to the fluid monitoring unit so as to activate the switch and wake the fluid monitoring unit, wherein, optionally, the fluid is sweat.

Aspects of the invention, such as, for example, the controller, may be implemented in digital electronic circuitry, or in computer hardware, firmware, software, or in combinations of them. Aspects of the invention may be implemented as a computer program or computer program product, i.e., a computer program tangibly embodied in an information carrier, e.g., in a machine-readable storage device or in a propagated signal, for execution by, or to control the operation of, one or more hardware modules. A computer program may be in the form of a stand-alone program, a computer program portion or more than one computer program and may be written in any form of programming language, including compiled or interpreted languages, and it may be deployed in any form, including as a stand-alone program or as a module, component, subroutine, or other unit suitable for use in a communication system environment. A computer program may be deployed to be executed on one module or on multiple modules at one site or distributed across multiple sites and interconnected by a communication network.

Aspects of the method steps of the invention may be performed by one or more programmable processors executing a computer program to perform functions of the invention by operating on input data and generating output. Aspects of the apparatus of the invention may be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

It may therefore be seen that embodiments of the present invention may provide means for minimising the overall power consumption of the electronics and efficiently managing the power consumed by the fluid monitoring electronics in accordance with the detection of fluids derived from the skin of the user, such as sweat.

BRIEF DESCRIPTION OF THE DRAWINGS

Embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION OF EMBODIMENTS

Figure 1:
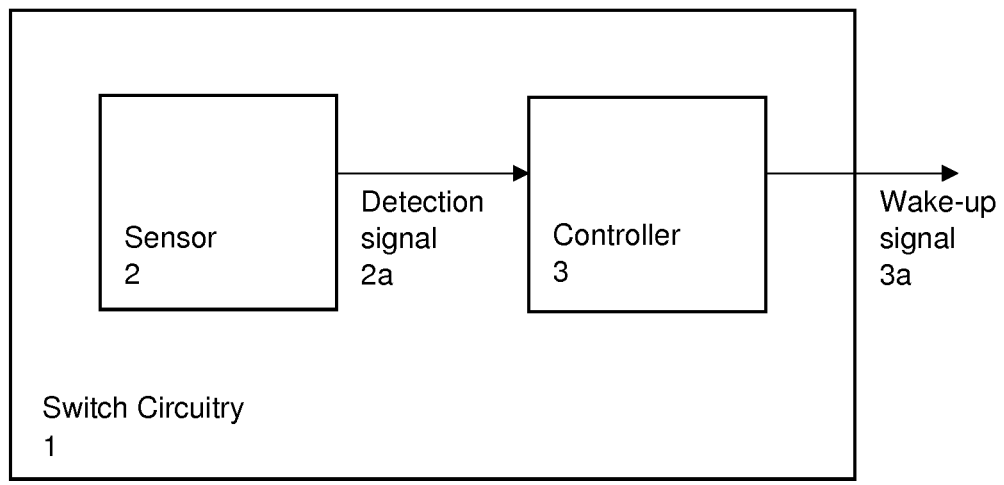
FIG. 1 is a block diagram of switch circuitry according to a general embodiment of the invention.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognise, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein may be used in the practice or testing of the embodiments.

As discussed above, continuous monitoring of biomarkers in fluids, such as sweat, can shed light on the health and wellbeing of an individual. However, fluid generation is not continuous or uniform and depends on the physical and mental state of the individual, i.e. it is a sporadic event. Having the fluid sensor (electronics for analysing and processing data, i.e. the fluid monitoring unit) continuously switched on, even when there are no fluid samples present, will lead to sub-optimal power utilisation of the system and hence lead to lower battery time. Consequently, frequent charging and/or replacement of the battery, and/or an increase in sensor device footprint is required.

The present invention relates to a system that generates a wake-up signal for the sensor electronics to perform fluid analysis only when there is fluid available at the fluid sensor site, as discussed above. By turning on the fluid sensor only when there is availability of fluid on the sensor site, the sensor device energy may be conserved during periods in which there is an absence of fluid samples. The battery time may therefore be prolonged and a smaller sensor device footprint may be achieved. The wake-up generation block is either self-powered (passive, without the need for additional active electronics) or consumes very low energy to operate. There may also be provided a configurable timing for wake-up signal generation that utilises a variable resistor to optimise the wake-up timing based on the rate of fluid generation.

FIG. 1 shows a block diagram of switch circuitry according to a general embodiment of the invention. The switch circuitry 1 comprises a sensor 2 and a controller 3. The sensor 2 is configured to detect fluid derived from the skin of a user and may be disposed in contact with the skin of the user so as to detect fluid excreted from the surface of the skin of the user. The fluid may preferably be sweat. The sensor 2 provides a detection signal 2a to the controller 3 in accordance with the detection of fluid. The controller 3 receives the detection signal from the sensor 2 and generates a wake-up signal 3a in response. The controller 3 provides the wake-up signal to a switch, which controls the power supplied to a fluid monitoring unit.

The natural secretion of fluids, such as sweat, in humans is sporadic and not uniform in time or periodic. As a consequence, powering the fluid monitoring unit when there is no fluid present will lead to unwanted expenditure in energy leading to sub-optimal utilisation of the fluid monitoring unit's power supply, such as, for example, a battery. Thus the power consumption of the fluid monitoring unit may be efficiently managed by controlling the power supplied to the electronics based on the detection of fluid.

Figure 2:
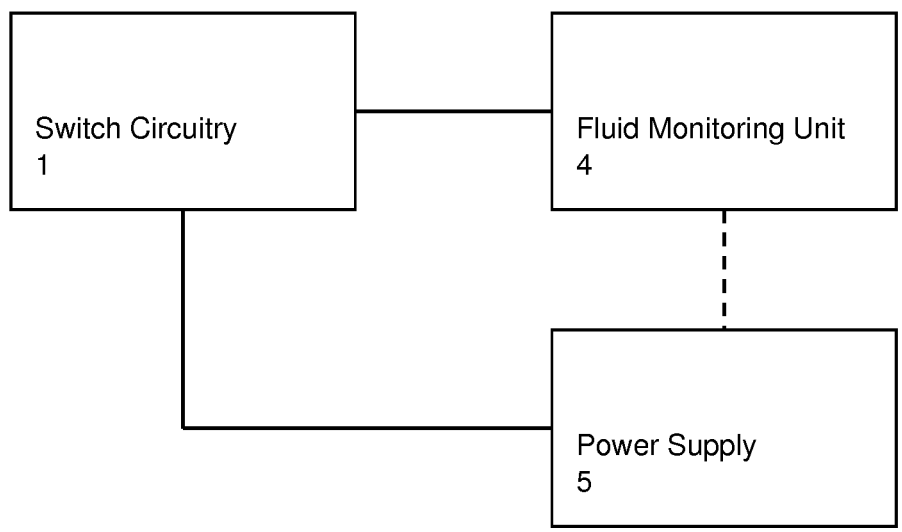
FIG. 2 is a block diagram of a system comprising the switch circuitry according to a general embodiment of the invention.

FIG. 2 shows a block diagram of a system comprising the switch circuitry according to a general embodiment of the invention. The system comprises the switch circuitry 1, a fluid monitoring unit 4 and a power supply 5. The connection between the fluid monitoring unit 4 and the power supply 5 is controlled by a switch that is activated and deactivated by the controller in the switch circuitry 1. That is, the power supplied to the fluid monitoring unit 4 is controlled by the switch. The specific positioning of the switch may vary and it may be provided as part of the switch circuitry 1, part of the fluid monitoring unit 4, part of the power supply 5 or as a separate entity disposed, for example, between the fluid monitoring unit 4 and the power supply 5. The switch circuitry 1 is connected to the fluid monitoring unit 4 and information may be transferred from the fluid monitoring unit 4 to the switch circuitry 1.

Figure 3:
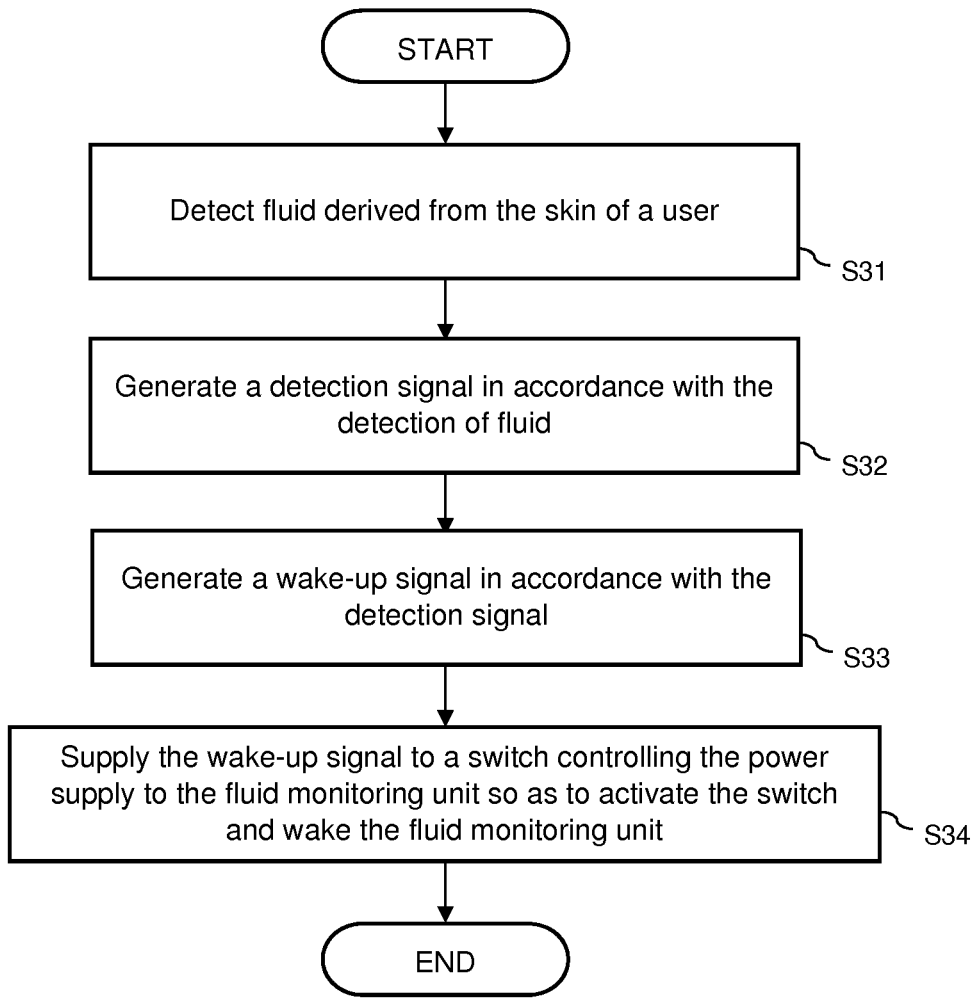
FIG. 3 is a flow chart of a method for controlling power supplied to a fluid monitoring unit according to a general embodiment of the invention.

FIG. 3 shows a flow chart of a method for controlling power supplied to a fluid monitoring unit according to a general embodiment of the invention. At step S31, fluid derived from the skin of a user is detected and a detection signal is generated in accordance with the detection of fluid at step S32. A wake-up signal is then generated in accordance with the detection signal at step S33. Finally, at step S34, the wake-up signal is supplied to a switch controlling the power supply to the fluid monitoring unit so as to activate the switch and wake the fluid monitoring unit.

As discussed above, embodiments of the invention may optimise the power consumption of the wearable fluid monitoring device (fluid monitoring unit), with a technique in which a passive wake-up switch may be placed between the battery and the electronics sub-system on the fluid monitoring device. The electronics sub-system is referred to as fluid monitoring electronics. The fluid monitoring electronics is the electronics sub-system which analyses the fluid sample and converts it into meaningful digital data. The switch, when turned-on, will provide the energy to the fluid monitoring electronics by connecting it to the power supply, such as a battery source and, when turned-off, will disconnect the power supply to the fluid monitoring electronics thereby conserving the energy in the battery. The wake-up switch is to be turned on at appropriate moments when fluid generation is active in the user so that the monitoring device may collect, process and analyse the fluid samples. Conversely, the switch is to be turned off where there is no presence of fluid or too little fluid at the measuring site. The fluid is any bodily fluid derived from the skin of the user, such as sweat, sebum, interstitial fluid. The fluid may preferably be sweat, such that the monitoring electronics are woken when sweat is detected by the sensor.

This turn-on/turn-off signal to activate/de-activate the wake-up switch is the wake-up signal. The wake-up signal may be generated in accordance with a sub-system (sensor) which uses bio-fuel cells that generate electrical energy in the presence of fluid, such as sweat. Alternatively, the wake-up signal may be generated in accordance with electrodes in the sub-system. The electrodes may be induction electrodes circumferentially placed around a flow channel of a microfluidic system of the sensor or ion-selective electrodes placed inside the flow channel. The generated electrical energy is used to wake-up the electronic sub-system of the monitoring device to perform analysis of the fluid samples.

By waking the power hungry fluid monitoring electronics only at times when sufficient fluid is present, the energy consumption may be optimised, thereby increasing the battery life and/or reducing the device footprint by using a smaller battery. The power consumption of the sub-system to generate the wake-up signal is very low and a configurable delay in waking-up the fluid monitoring electronics based on the rate of fluid generation may be provided.

Figure 4:
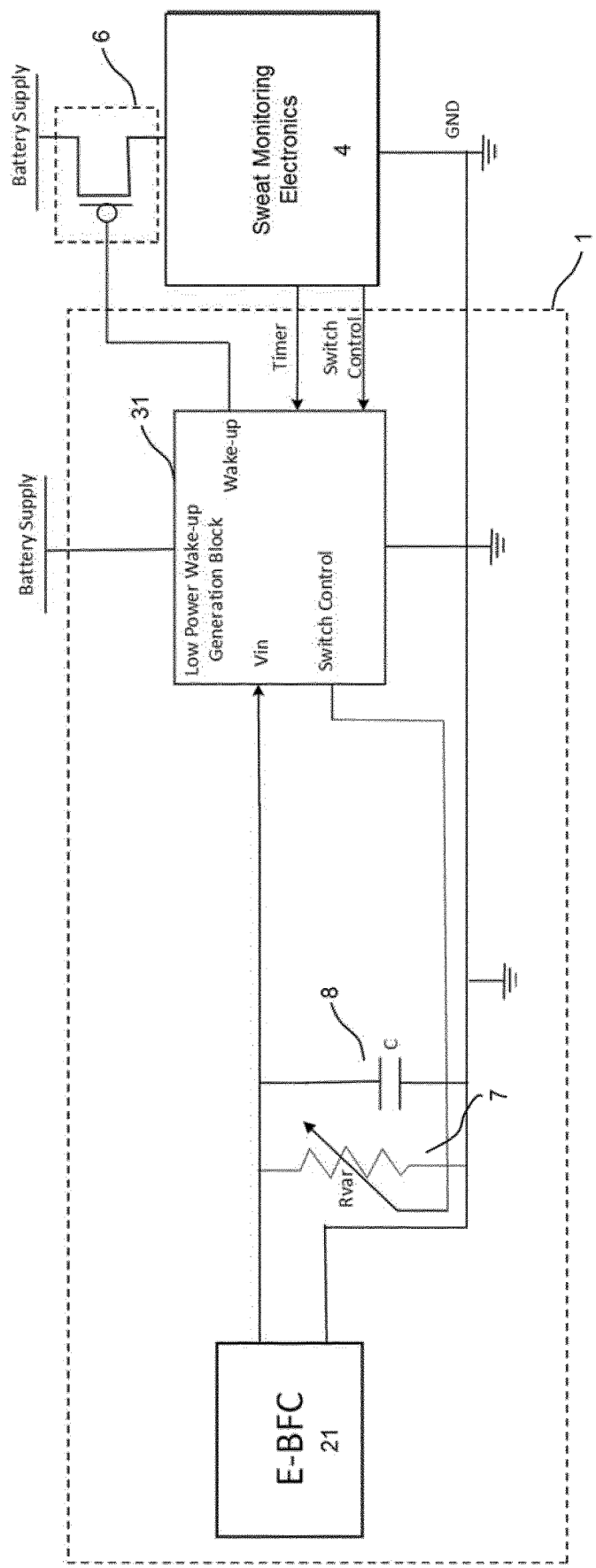
FIG. 4 is a circuit diagram of a system comprising switch circuitry according to an embodiment of an aspect of the invention.

FIG. 4 is a circuit diagram of a system comprising switch circuitry according to an embodiment of an aspect of the invention. More specifically, FIG. 4 shows a schematic overview of a wake-up generation system based on sweat production rate with configurable delay for optimal wake-up timing. The sensor in this embodiment is an electrochemical sensor, specifically, an electronic skin based bio fuel cell (E-BFC). E-BFCs are known in the art and are capable of converting human sweat into significant electrical energy capable of powering a radio communication device. For example, an E-BFC capable of charging a 2.2 mF capacitor to 3.5V in 53 seconds is known. Such an E-BFC may be used to provide a wake-up signal and switch on the sweat monitoring electronics once the sweat generation is active in the individual using a sensor which may be provided as part of the sweat monitoring patch. That is, the E-BFC may be provided as part of a patch that is applied/attached to the skin of the user. Thus the wake-up generation system uses sweat samples resulting from the detection of sweat at the E-BFC to form an active biofluid cell.

The circuit shown in FIG. 4 comprises the E-BFC 21, a low power wake-up generation block 31 (controller), sweat monitoring electronics 4 and a switch 6. A variable resistor 7 and capacitor 8 are connected in parallel across the output of the E-BFC 21.

The E-BFC 21 is the skin based bio-fuel cell which generates an electrical voltage in response to sweat. The value of the generated voltage depends on the amount of sweat present at the site where the E-BFC 21 is in contact with the skin of the user. A constant sweat generation will yield a constant voltage at the output of the E-BFC 21. The open source voltage is then connected to the variable resistor 7 and the capacitor 8. The variable resistor 7 provides dynamic resistance to the output of the E-BFC 21. Specifically, by varying the resistive load (i.e. the value of the variable resistor 7), a re-configurable delay for the capacitor 8 voltage Vin to reach a set threshold value Vth may be provided. This allows for better control of the amount of sweat required to wake-up the system and the delay may be configured for different sweat rates. The variable resistor 7 may be provided as a transistor, such as a MOSFET, and the resistance may be varied by controlling the gate voltage of the transistor. The switch control signal is applied from the Low Power Wake-up Generation Block to control the variable resistor. The switch control signal for the resistor 7 may be set by the sweat monitoring electronics 4 based on, for example, the sweat rate of the user and/or other parameters, such as properties or measurements of the sweat. The variable RC at the output of the E-BFC 21 also helps in removing transient peaks in Vin which may generate false wake-up triggers when there is not sufficient sweat present.

The low power wake-up generation block 31 receives the signal Vin from the E-BFC 21 and the capacitor 8. A timer signal and control signal from the sweat monitoring electronics 4 are also input to the low power wake-up generation block 31. When the sweat monitoring electronics 4 are in an active mode (i.e. not asleep), a control signal providing the switch control information to configure the variable resistor 7 is delivered to the low power wake-up generation block 31, so that the low power wake-up generation block 31 may control the value of the resistor 7 in accordance with the switch control.

The wake-up signal is delivered to the switch 6 from the low power wake-up generation block 31, in accordance with Vin received from the E-BFC and the capacitor 8. The wake-up signal may be considered as a high or low logic signal which activates (closes) or deactivates (opens) the switch 6 and may be derived as NOT(Vtrigger OR Vtimer), where NOT represents a logical negation and OR represents logical 'anding' of digital signals.

When the Vin signal exceeds a threshold voltage Vth, the Vtrigger signal is set to logical 'high'. Vtimer is the value of the "Timer" signal, which defines a time period to expire before the sweat monitoring electronics 4 switch to a sleep mode. So when the sweat monitoring electronics 4 switch to the sleep mode, the timer signal is set to logical 'low' and hence Vtimer is set to logical 'low'.

When there is insufficient sweat generated at the E-BFC, Vin does not exceed Vth and Vtrigger is set to logical 'low'. The wake-up signal supplied to the switch 6 is therefore set at logical 'high', which opens the switch 6 and shuts down the monitoring electronics 4. Once there is enough sweat present at the E-BFC, Vin passes Vth and so Vtrigger is set to logical 'high'. The wake-up signal is therefore set to logical low and the switch 6 is closed to wake the monitoring electronics 4. When woken, the monitoring electronics 4 set the timer signal 'high' thereby setting Vtimer 'high'. This ensures that once the monitoring electronics are woken, they are able to determine when to go back to sleep. That is, the timer sets a minimum period of time that the sweat monitoring electronics 4 are awake, such that they are not disconnected from the power supply during analysis of the sweat. Setting Vtimer 'high' ensures that power is maintained to the sweat monitoring unit 4 irrespective of the value of Vtrigger.

Once the monitoring electronics have finished the relevant processing, Vtimer is set low. If Vtrigger is also low due to unavailability of sweat, then the wake-up signal is high and the switch 6 is opened triggering the shutdown of the monitoring electronics 4. The logic table below (Table 1) shows the relationship between Vtrigger, Vtimer, the wake up signal and the resulting status of the sweat monitoring electronics. This is based on the logic relationship NOT (Vtrigger OR Vtimer) described above.

TABLE 1

Exemplary logic table and resultant control of circuit components

| Vtrigger | Vtimer | Wake-Up Signal | Switch | Monitoring Electronics |
| --- | --- | --- | --- | --- |
| 0 | 0 | 1 | Open | Sleep |
| 0 | 1 | 0 | Closed | Awake |
| 1 | 0 | 0 | Closed | Awake |
| 1 | 1 | 0 | Closed | Awake |

The low-power wake-up generation block 31 is always 'on' thereby consuming active energy. However, this energy is much lower than the energy that would be expended if the sweat monitoring electronics 4 were constantly active, even without any sweat present. By activating the sweat monitoring electronics 4 specifically at moments when there is (sufficient) sweat present, the battery of the sweat monitoring system may be persevered and its life extended. The resistance of the variable load resistor 7 is set to a very low value after every successful measurement cycle so as to discharge the load capacitor 8 and prepare the circuit for the next cycle. A measurement cycle corresponds to a period of time when the sweat is being analysed by the sweat monitoring electronics. The value of the resistor 7 may be set low before being set to a value corresponding to the switch control set by the sweat monitoring electronics in accordance with the requirements of the system and/or the user.

Figure 5:
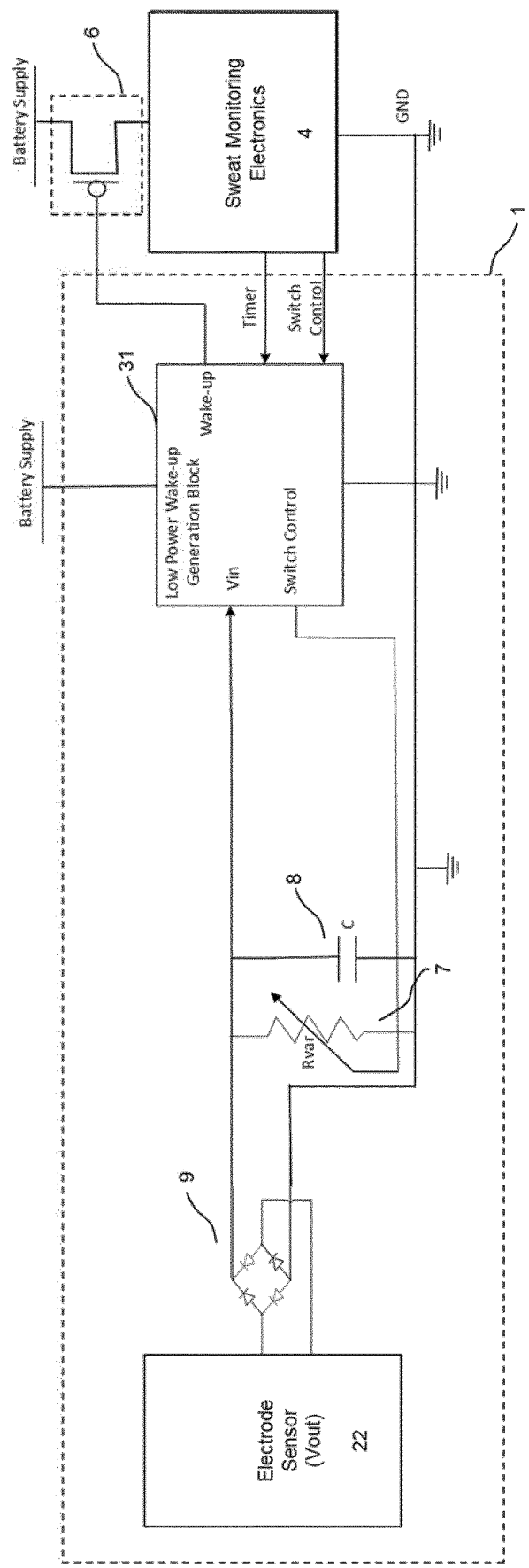
FIG. 5 is a circuit diagram of a system comprising switch circuitry according to an embodiment of an aspect of the invention.

FIG. 5 shows a circuit diagram of a system comprising switch circuitry according to another embodiment of an aspect of the invention. FIG. 5 is the same as FIG. 4, with the exception of the sensor in which an electrode sensor 22 replaces the E-BFC from FIG. 4. Furthermore, a full bridge rectifier 9 is connected across the output of the electrode sensor 22. The electrode sensor 22 utilises electricity induced in electrodes by moving ions in the sweat. Thus, similarly to the E-BFC, the electrode sensor 22 generates an electric potential when sweat is present at the sample site. This potential may then be used to trigger waking of the sweat monitoring electronics 4.

As discussed above, a liquid triboelectric generator/sensor based detection signal may be used to trigger the waking of the sweat monitoring electronics. The working mechanism of the liquid triboelectric generator/sensor is based on two simultaneous effects: contact electrification (triboelectric charging) and electrostatic induction. In this case, the flow of sweat through the channel (which may be, for example, silicone or PTFE based) and over the sensing surface generates a frictional drag force, which, in combination with ions present in sweat (enhancing the signal), causes local charge (electric field) re-distribution/imbalance around the electrodes (liquid electrostatic induction) eventually inducing an electric potential difference between the two induction electrodes and drives electrons to flow from one electrode to the other electrode.

In an alternative arrangement, a detection signal produced by ion-selective electrodes placed inside the fluid channel is used to trigger waking the sweat monitoring electronics. As with all well-known potentiometric ion sensors, an ion-selective membrane is provided as a key component. The ion-selective membrane establishes the preference with which the sensor responds to an analyte in a sample, from among various interfering ions that are also present in the sample. An electrochemical equilibrium can be reached if ions are able to penetrate the boundary between two phases, with different potentials in the two phases formed when equilibrium is established. However, if only one type of an ion is able to be exchanged between the two phases, then the potential difference formed between the phases is determined solely by the activities of the one type of ion in the phases. If an ion-selective membrane which is only permeable to the one type of ion is used to separate two solutions of different ionic activities, then the potential difference across the membrane may be defined by a Nernst equation.

The electrode sensor 22 may comprise a flow channel and induction electrodes arranged circumferentially around the outer lumen of the flow channel. The induction electrodes generate a triboelectric potential due to moving ions in the sweat flowing through the flow channel. Alternatively, the electrode sensor may comprise a flow channel and ion-selective electrodes arranged inside the flow channel. The ion-selective electrodes generate an electrochemical potential due to moving ions in the sweat flowing through the flow channel, as discussed above. When induction electrodes (triboelectric potential) are used in the sensor, at least one electrode is provided which is measured against ground. There may preferably be at least two electrodes to measure differentially. When ion-selective electrodes (electrochemical potential) are used in the sensor, at least one electrode is provided which is measured against a reference electrode potential, similarly, for example, to a simple pH measurement probe.

The electric potential generated by moving ions is therefore used for the wake-up of the sweat monitoring electronics 4 so as to measure, on-demand, only when new sweat is produced by the user and detected at the sensor. The wake-up generation system therefore synchronises sensor measurement events, by the sweat monitoring electronics 4, with the sweat production rate, using 'self-generating' wake up signal from the electrode sensor 22.

Using the electrodes in the sensor, once new sweat is produced the (initially) transient or pulsatile sweat flow/pressure wave (moving ions) through the microfluidic system generates a liquid triboelectric or electrochemical potential (transient signal) which is used to wake up the sweat monitoring unit. The produced signal is harvested by the induction electrodes circumferentially placed around or ion-selective electrodes inside the flow channel of the microfluidic system.

Figure 6:
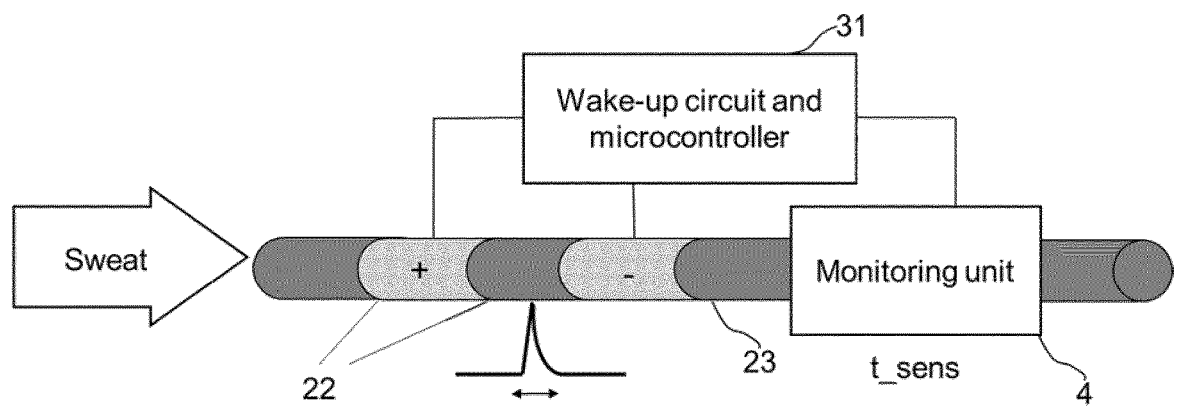
FIG. 6 is a diagram of electrodes and a flow channel in the system according to an embodiment of an aspect of the invention.

FIG. 6 shows a diagram of the electrodes and flow channel with respect to the other system elements according to an embodiment of an aspect of the invention. The system comprises a flow channel 23 and an electrode sensor 22 with electrodes that are either induction electrodes circumferentially arranged outside the channel 23, or ion-selective electrodes inside the channel 23. Sweat excreted by the user flows into the flow channel 23. Sweat may be considered as moving ions in water and the ions interact with the electrodes 22 to generate a potential. The sweat may include, for example, sodium ions Na+, hydroxide ions OH−, chloride ions Cl− and/or hydrogen ions H+. The use of induction electrodes therefore provides a sweat based wake-up signal generation system with passive circuit with self-generating wake-up signal generated from moving ions and transmitted through induction or ion-selective electrodes.

The generated potential is provided to the wake-up circuit and microcontroller 32, which in turn wakes the monitoring unit 4. The wake-up circuit and microcontroller 32 may be comparable in function to the low power wake-up generation block 31 and switch 6 of FIG. 5. The flow channel 23 continues through the monitoring unit 4 such that the sweat used to wake the monitoring unit 4 may pass through the unit 4 for analysis when the unit 4 is awake. The monitoring unit 4 may also be considered as a fluid sensor or bio-analyser unit that analyses the composition or biomarkers of sweat. The monitoring unit 4 is in a sleep mode prior to generation of the potential at the electrodes 22.

Once a steady sweat flow is established, the system continues to measure. The frequency in the periodicity of the transient event (duty cycle) and/or time-derivative in the signal produced (changes in flow over time) at the electrodes may be monitored and used to shut down the device, i.e. switch the monitoring unit to a sleep mode. For example, if the triboelectric signal has not changed considerably over time (such as, for example 10 minutes), the device is set back into sleep mode by the controller.

According to an aspect, a liquid triboelectric generator may be used to generate the detection signal. It is known for such a generator to be implemented in a pipette tip to measure electrolyte concentrations. Depending on NaCl solution volume (20-100 μL), NaCl concentration (0-500 mM) and temperature (20-60° C.), open circuit voltages of about 1-2V and current in the order up to 15 μA were measured. Typical Na+ and Cl− concentrations in sweat are 50-70 mM. Information on a triboelectric signal generation may be found at: https://www.sciencedirect.com/science/article/pii/S2211285517303750.

In a wake up system with triboelectric charge induction electrodes, the voltage difference between the electrode pair is measured by an amplifier having a very large input impedance (for example, 200Ω), as the triboelectric signal typically has a high optimum output impedance which needs to be matched and converted to a suitable wake-up current using power conversion electronics. This signal is typically an alternating signal (AC) which may need to be rectified before being utilised by the wake-up electronics. An appropriate rectifier is shown in the circuit diagram of FIG. 5.

Figure 7:
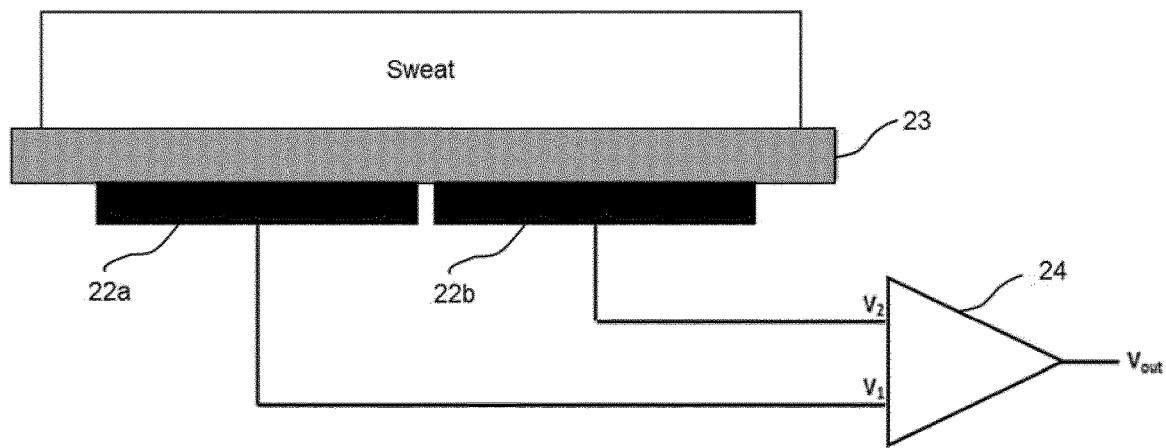
FIG. 7 is a block diagram of induction electrodes to generate the detection signal according to an embodiment of an aspect of the invention.

FIG. 7 shows a cross-section of induction electrodes according to an embodiment of an aspect of the invention. A first induction electrode 22a and a second induction electrode 22b are connected to an amplifier 24, with a fluid channel 23 provided in cooperation with the induction electrodes. A cross-section of the fluid channel 23 is shown in FIG. 7, which may be formed from silicone, PTFE or the like. Sweat may be provided across the first induction electrode 22a and the second induction electrode 22b, with the sweat comprising moving ions. A triboelectric potential is generated through the moving ions. The first induction electrode 22a and the second induction electrode 22b may be formed of copper. The amplifier 24 has a very large input impedance, for example, 200 TΩ. The voltage difference between the two induction electrodes 22a, 22b around a fluid channel is measured by the amplifier 24. The first induction electrode 22a may be a positive electrode and the second induction electrode 22b may be a reference or grounded electrode. Output signals are mostly AC signals and so rectification may be required. Thus, the output of the amplifier Vout may be rectified (for example, half or full bridge rectification) and then provided to the controller to generate the wake-up signal.

According to an embodiment of another aspect of the invention, the concentration of lactate in the sweat may be used to wake the sweat monitoring unit. That is, lactate oxidase may be used as an E-BFC. The circuitry for this embodiment is the same as that shown in FIG. 4, with the exception of the E-BFC which generates the detection signal based on the lactate concentration. Thus, the difference between the embodiment shown in FIG. 5 and this embodiment is that the wake-up signal is generated in response to the lactate concentration exceeding a threshold, rather than when sweat (or an amount of sweat) is detected. By integration of the enzyme lactate oxidase with the anode of the E-BFC, the energy output is directly related to the concentration of lactate in the sweat. This enables the activation of the sweat monitoring electronics when a specific concentration of lactate is available in the sweat.

Figure 8:
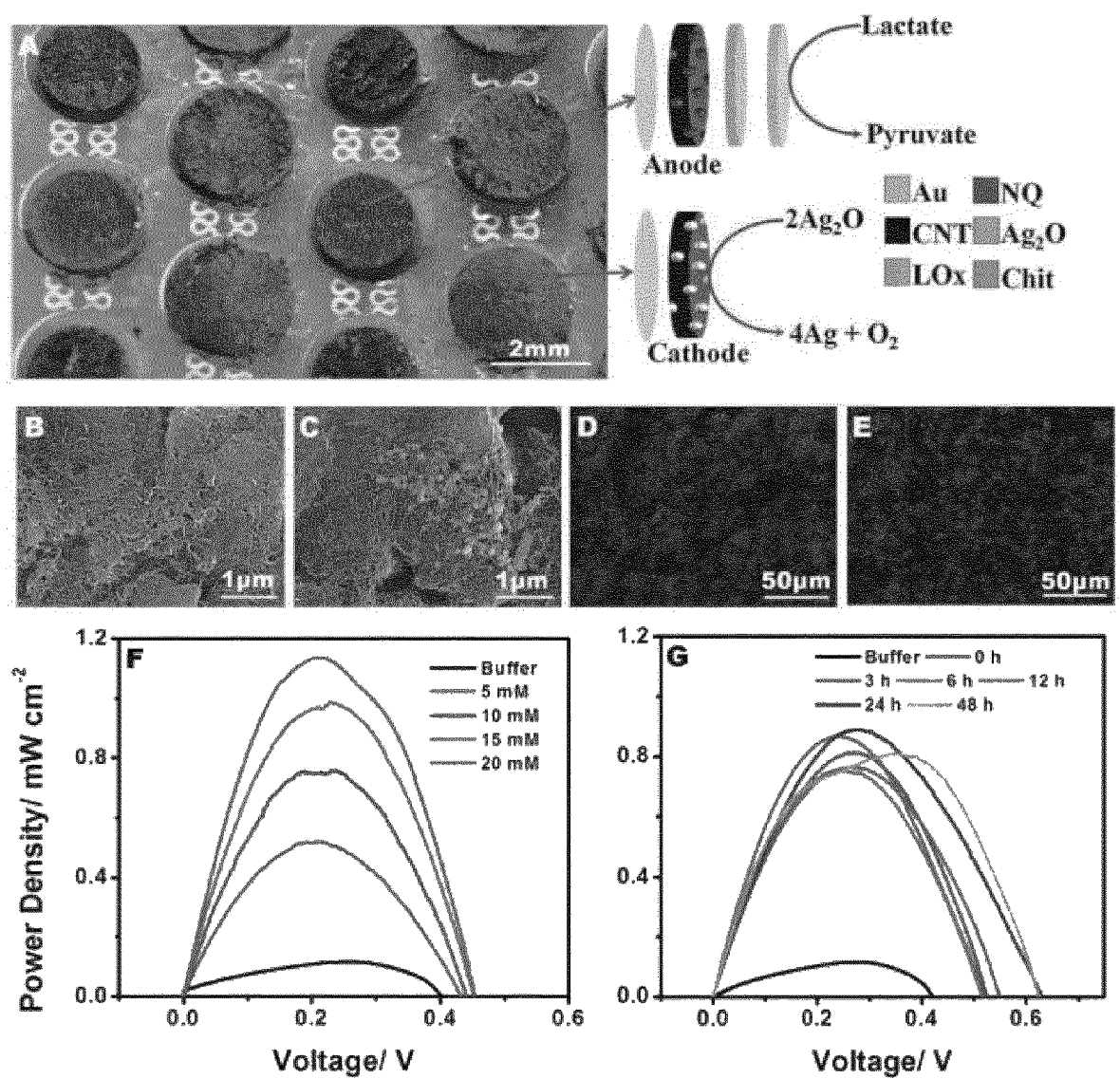
FIG. 8 is a diagram of the E-BFC and resulting voltage generation according to an embodiment of an aspect of the invention.

FIG. 8 shows diagrams of the reactions occurring at the anode and cathode of the E-BFC according to the embodiment and the resulting voltage generation.

Since lactate is a sepsis marker (an indicator of sepsis), any increase of lactate is a reason to generate an alert during the monitoring of the patient. Thus, the high concentration of lactate may generate enough voltage to wake-up the patch and/or sensor that may enable a direct communication to generate an alert or notification. It may also, additionally or alternatively, enable a sensor to acquire any additional measurements so as to verify the reading and reduce the amount of false positives. That is, detection of lactate may provide a wake-up signal or an alert if the generated voltage at the E-BFC exceeds a threshold value indicating that the lactate is too high. As well as considering the concentration of lactate in the sweat, a change in the concentration of lactate may also be used. For example, if the lactate concentration does not deviate from a predetermined level by at least a predetermined amount for a predetermined amount of time (i.e. the concentration does not deviate from a certain amount over a period of time), the detection signal may not be generated and the monitoring unit may remain inactive.

Figure 9:
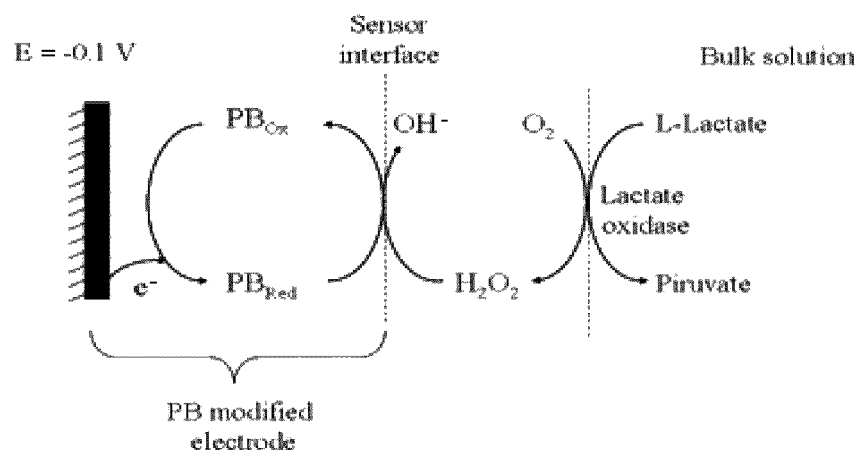
FIG. 9 is a diagram showing the conversion of lactate into pyruvate.

As mentioned above the enzyme lactate oxidase converts the lactate (substrate) into pyruvate (product). This conversion of lactate into pyruvate is shown in FIG. 9. This conversion is responsible for the energy generation. The approach is similar to electrochemical bio sensors and thus enzymes used in these kind of sensors may also be used to enable energy generation specifically for other molecules of interest. Such enzymes may include, for example, glucose oxidase, choline oxidase, cholesterol oxidase, D-amino and L-amino acid oxidase, alcohol oxidase, uricase, lactate oxidase, xanthine oxidase, bilirubin oxidase, glutamate oxidase, putrescine oxidase and polyamine oxidase. A wake-up signal may therefore be generated in response to the detection of such enzymes exceeding a threshold.

As may be seen from the above, embodiments of the present invention may provide switch circuitry for controlling power supplied to a sweat monitoring device in accordance with the detection of sweat. The power consumption of the device may be minimised and efficiently managed.

Although only a few exemplary embodiments have been described in detail above, those skilled in the art will readily appreciate that many modifications are possible in the exemplary embodiments without materially departing from the novel teachings and advantages of the embodiments of the present disclosure. The above-described embodiments of the present invention may advantageously be used independently of any other of the embodiments or in any feasible combination with one or more others of the embodiments.

Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements. In a device or apparatus claim enumerating several means, several of these means may be embodied by one and the same item of hardware. The mere fact that certain measures are recited in mutually different dependent claims does not indicate that a combination of these measures cannot be used to an advantage.

The invention claimed is:

1. A switch circuitry for controlling power supplied to a fluid monitoring unit, the switch circuitry comprising:
   a sensor configured to detect fluid derived from the skin of a user and to generate a detection signal in accordance with detection of fluid; and
   a controller configured to receive the detection signal, to generate a wake-up signal in accordance with the detection signal, and to supply the wake-up signal to a switch controlling the power supply to the fluid monitoring unit so as to activate the switch and wake the fluid monitoring unit,
   wherein
   the sensor is configured to:
      detect a first amount of fluid at a first time point;
      detect a second amount of the fluid at a second time point occurring after the first time point;
      calculate a difference between the first amount of fluid and the second amount of fluid; and
      generate the detection signal when the difference between the first amount of fluid and the second amount of fluid exceeds a predetermined threshold.

2. The switch circuitry according to claim 1, wherein
   the fluid monitoring unit is configured to generate a timer signal indicating a timer delay in response to receiving the wake-up signal and to supply the timer signal to the controller; and
   the controller is configured to supply the wake-up signal to the switch for the duration of the timer delay indicated by the timer signal so as to maintain activation of the fluid monitoring unit for at least the duration of the timer delay.

3. The switch circuitry according to claim 1, wherein the sensor is configured to generate the detection signal in response to detecting a predetermined amount of fluid for a predetermined amount of time.

4. The switch circuitry according to claim 1, comprising a notification unit configured to receive the wake-up signal and to generate an alarm in response to receiving the wake-up signal.

5. The switch circuitry according to claim 1, wherein the sensor is configured to be positioned in direct contact with the skin of a user so as to detect fluid excreted from the skin of the user.

6. The switch circuitry according to claim 1, wherein the sensor is configured to:
   measure a concentration of a substrate in the detected fluid; and
   generate the detection signal when the concentration of the substrate in the detected fluid exceeds a predetermined threshold.

7. The switch circuitry according to claim 1, comprising:
   a variable resistor connected in parallel with the sensor; and
   a capacitor connected in parallel with the variable resistor, wherein
   the variable resistor and the capacitor are configured to control the delivery of the detection signal to the controller.

8. The switch circuitry according to claim 7, wherein the controller is configured to control the value of the variable resistor in accordance with parameters received from the fluid monitoring unit when the fluid monitoring unit is active.

9. The switch circuitry according to claim 7, wherein the controller is configured to temporarily set the variable resistor to a minimum value prior to deactivating the switch so as to discharge the capacitor.

10. The switch circuitry according to claim 1, wherein:
    the sensor is an electronic skin based bio-fuel cell, E-BFC, configured to generate an electric potential in response to the detection of fluid; and
    the generated electric potential corresponds to the amount of fluid detected.

11. The switch circuitry according to claim 10, wherein the E-BFC is configured to generate the detection signal when the generated electric potential exceeds a predetermined threshold corresponding to the detection of a given amount of fluid.

12. The switch circuitry according to claim 1, wherein the sensor comprises:
    a flow channel arranged such that fluid flows through the flow channel; and
    an induction electrode arranged circumferentially around the periphery of the flow channel and configured to generate a triboelectric potential due to moving ions in the fluid flowing through the flow channel; and
    wherein:
       the triboelectric potential generated by the induction electrode corresponds to the rate or concentration of moving ions in the fluid flowing through the flow channel; and
       the induction electrode is configured to generate the detection signal when the generated triboelectric potential exceeds a predetermined threshold corresponding to a given rate of moving ions.

13. The switch circuitry according to claim 1, wherein the sensor comprises:
    a flow channel arranged such that fluid flows through the flow channel; and
    an ion-selective electrode arranged inside the flow channel and configured to generate an electrochemical potential due to moving ions in the fluid flowing through the flow channel; and
    wherein:
       the electrochemical potential generated by the ion-selective electrode corresponds to the rate or concentration of moving ions in the fluid flowing through the flow channel; and the ion-selective electrode is configured to generate the detection signal when the generated electrochemical potential exceeds a predetermined threshold corresponding to a given rate of moving ions.

14. A method of controlling power to a fluid monitoring unit, the method comprising:

detecting fluid derived from the skin of a user;

generating a detection signal in accordance with the detection of fluid;

generating a wake-up signal in accordance with the detection signal; and supplying the wake-up signal to a switch controlling the power supply to the fluid monitoring unit so as to activate the switch and wake the fluid monitoring unit, wherein the detecting comprises:

detecting a first amount of fluid at a first time point; and detecting a second amount of the fluid at a second time point occurring after the first time point; and wherein the generating comprises:

calculating a difference between the first amount of fluid and the second amount of fluid; and generating the detection signal when the difference between the first amount of fluid and the second amount of fluid exceeds a predetermined threshold.

* * * * *